(12) United States Patent
Broselid

(10) Patent No.: US 6,280,405 B1  
(45) Date of Patent: Aug. 28, 2001

(54) DEVICE FOR STATIONARY AND/OR AMBULANT TRACTION OF THE SPINAL COLUMN

(75) Inventor: Jan Broselid, Färjestaden (SE)

(73) Assignee: Fisheries Management and Supply Co A.B. (SE)

(*) Notice: Subject to any disclaimer, the term of this patent is extended or adjusted under 35 U.S.C. 154(b) by 0 days.

(21) Appl. No.: 09/402,951
(22) PCT Filed: Dec. 3, 1996
(86) PCT No.: PCT/SE96/01587
  § 371 Date: Oct. 12, 1999
  § 102(e) Date: Oct. 12, 1999
(87) PCT Pub. No.: WO97/20528
  PCT Pub. Date: Jun. 12, 1997
(51) Int. Cl.[7] .......................................................... A61F 5/00
(52) U.S. Cl. .................. 602/36; 602/19; 128/874
(58) Field of Search ................................. 128/845, 846, 128/869, 873, 874, 875, 876; 602/5, 19, 36

(56) References Cited

U.S. PATENT DOCUMENTS

| | | |
|---|---|---|
| 2,835,247 | 5/1958 | Stabholc . |
| 2,886,031 | 5/1959 | Robbins . |
| 3,548,817 | 12/1970 | Mittasch . |
| 4,622,957 | 11/1986 | Curlee . |
| 4,715,362 | 12/1987 | Scott . |
| 4,721,102 | 1/1988 | Pethybridge . |
| 5,405,313 | 4/1995 | Albin . |
| 5,462,518 | 10/1995 | Hatley et al. . |

*Primary Examiner*—Michael A. Brown
(74) *Attorney, Agent, or Firm*—Fasth Law Offices; Rolf Fasth

(57) ABSTRACT

A device for applying traction to, and/or relieving part of the pressure on, the human spinal column, including a lower, adjustable harness (2), being supported against the patient's pelvis/hipbone, an upper, adjustable harness (1) taking support around the patient's shoulders and under the arm pits, thus applying traction to a maximum number of the vertebrae via keybones and shoulder blades, and elastic force elements (3), striving to separate the two harnesses, symmetrically arranged between said harnesses, on both sides of the spine, said elastic force elements all being located on the front side of the patient's body and including at least two gas springs (3) having the same, pre-selectable, nearly stroke-independent force, and being symmetrically located on each side of, and equally spaced from, the body symmetry plane through the spine.

3 Claims, 4 Drawing Sheets

DEVICE FOR STATIONARY AND/OR AMBULANT TRACTION OF THE SPINAL COLUMN

Figure 1:
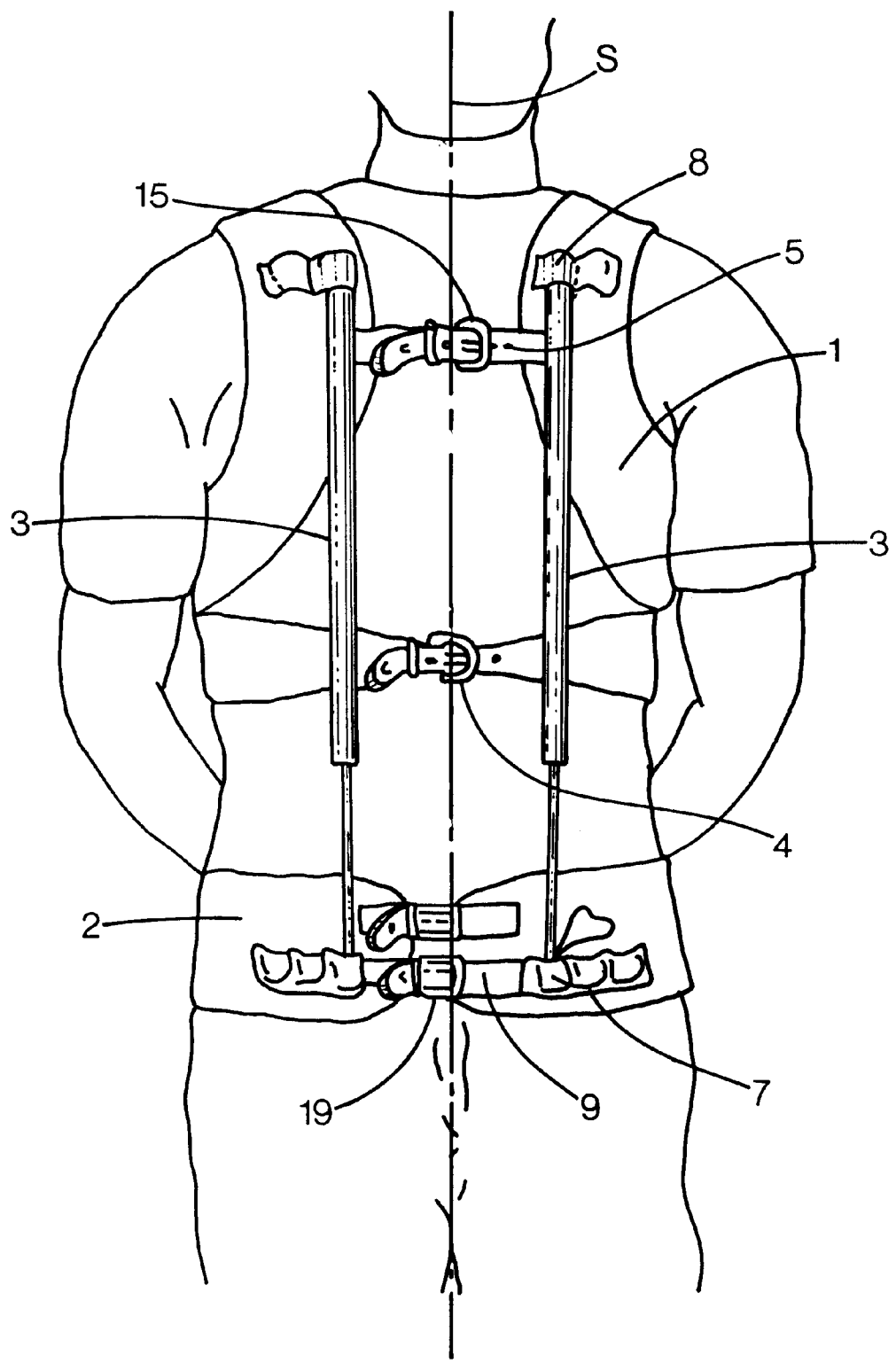

This application is a 371 of PCT/SE96/01587 filed Dec. 3, 1996.

TECHNICAL AREA

The present invention relates to an improved device for traction of the human spinal column, for preventive purposes and as medical treatment, and for relieving forces from said spinal column, and which may be used also while the patients are moving around in an upright position.

STATE OF THE ART

Since at least 50 years, spinal ailments have been treated, with varying success, with the aid of traction of the spinal column, performed in various ways. Earlier, this traction treatment demanded that the patient be lying in bed, while traction forces were applied onto the patient's spine by means of wires connected to various parts of the body, said wires being tightened through weight or spring loading.

Also known, are treatments where the patient is sitting in a chair with a vertically arranged traction system, whereby the patient is able to move his arms during the treatment procedure, but no other mobility is possible. Later, some systems have also been presented which allow the patient to walk and to stand upright, while the traction is applied by means of fixed mechanical, adjustable devices, the length of which can be adjusted, see for example U.S. Pat. No. 2,835,247. This device is, however, far too bulky and cumbersome in practice for the patient to be able to dress in normal clothes and move around freely.

Devices where mechanical springs have been used to provide the traction are also known, for example from U.S. Pat. No. 2,886,031. This device is however impaired by the disadvantage of allowing forward bending of the spine, as the upper strut mountings are located too close to the spinal column, and this is totally inappropriate for some ailments. The basic version of this device has no resilient components at all, whilst a modification exhibits resilient support. However, the upper strut mountings are located to close to the spinal column to allow the patient to perform active self-traction by using his/her abdominal muscles. Furthermore, this device is largely designed from hard materials like metal, which are uncomfortable to the body.

U.S. Pat. No. 4,721,102 describes an apparatus comprising two belts to be tightened around the abdomen. Between these belts, spaced around the body in a number of locations, short coil springs are provided. This device has the disadvantage of only allowing treatment of a short part of the spinal column. Furthermore, it is uncomfortable to lie down on. U.S. Pat. No. 3,548,817 describes a similar device having the same drawbacks.

The patent U.S. Pat. No. 4,715,362 describes a device comprising two belts, one being supported by the patient's pelvis and the other around the chest below the arms. Between these belts there are several resilient force elements, all located on the patient's backside. The elements can be length adjusted by screwing, in order to fit the body shape of different patients and achieve suitable traction, and the pre-setting forces are varied by increasing or decreasing the number of active coil turns. Also this device has a number of weaknesses. For example, all the coil elements are located on the backside of the body. This means that a patient carrying this device tends to become stooping and forward bent. Also, due to the location of the suspension elements, the patient cannot practice any active self-traction by tensing his/her abdominal muscles. The spring devices are stated as being used for the relieving of shocks that might otherwise load the spinal column, and are thus apparently not contemplated to be used for providing traction, i.e. in such a manner that a mechanical setting of the length of the resilient elements will determine the static traction. This entails the spring forces having to be so high that the patient will generally experience the device as rigid. Furthermore, this device makes it difficult and uncomfortable for the patient to rest lying down on his/her back, and makes it difficult for the staff to attach the device onto a patient lying down, without turning the patient around. The longitudinal adjustment, necessary for adaptation of the device to different patients, demands a certain care and takes time, and for a patient needing many spring packages, the weight might cause discomfort.

The resilient devices described above also have the major disadvantage in common, that their resilient elements consist of mechanical springs. The force of these mechanical springs will vary substantially with their compression. This is because their force is a linear function of the change in compression, and will increase or decrease by a more or less high constant factor (the spring constant). This makes the device very sensitive to position changes, which means that if the patient puts the device on in a manner such that the distance between the belts will vary somewhat from time to time, the traction force will vary substantially. The same applies when the patient bends, e.g. sideways. The force will then increase substantially on one side of the body whilst decreasing in a corresponding degree on the other. As a suitable traction force for each patient is determined by a doctor and/or a therapist, etc., and the effect of the treatment may be highly dependent on maintaining the appropriate force, then this weakness is obvious, as a change in force is very unsuitable for certain ailments.

The two devices according to U.S. Pat. Nos. 4,721,102 and 3,548,817 have, due to the short springs, the same disadvantage regarding the characteristics of the mechanical springs as mentioned above, but to a still higher degree.

U.S. Pat. No. 5,405,313 shows a rigid fixing harness having no flexible elements at all. The upper portion of the chest-shoulder harness is, on the backside, anchored in the lower pelvic harness and will rather cause a contraction of the spinal column, whilst the rigid adjustable struts running between the rear side of a pelvic belt and the front side of the arm pits are creating a tractional effect. The sum of this is mainly that the harness will hold the spinal column fixed, whereas the shoulders are rather exposed to a rearwards turning force. There is no possibility of active self-traction through using the abdominal muscles.

SUMMARY OF THE INVENTION

Consequently, there exists a need for improving the existing devices for traction and relief of the spinal column, so as to improve the function and reduce the force variations, to enable traction on the largest possible section of the spinal column, to make the device simpler to adjust and to put on, whilst needing less precision in order to achieve the correct traction force and being lighter and more comfortable to carry in a standing, sitting as well as a lying position. There is also a need for a device that is sufficiently comfortable to carry, to enable its use for preventive relief of the spinal column of persons having back problems and working in vibrating vehicles, such as dumpers and excavators.

Furthermore, there is a need for a device allowing the bearer to actively stretch his spinal column in a simple way (for the purposes of this description called self-traction).

The object of the invention is thus to provide a traction device for the human spinal column which fulfils the aforementioned requirements.

This is achieved, according to the invention, by a portable traction device, the characteristics of which are defined by the accompanying patent claims, whereby the dependent claims describe preferred embodiment forms.

DETAILED DESCRIPTION OF THE INVENTION

Figure 2:
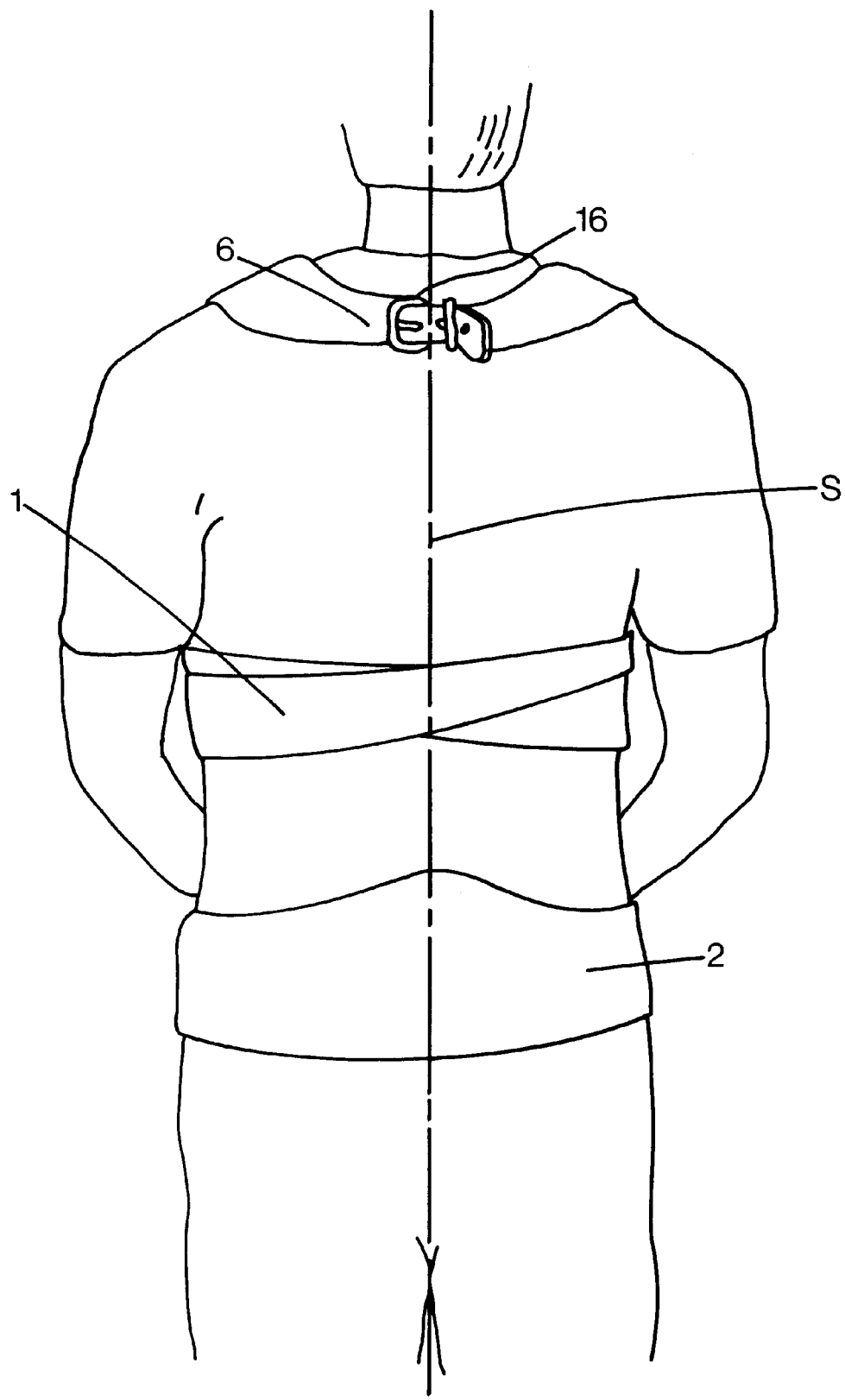
Figure 3:
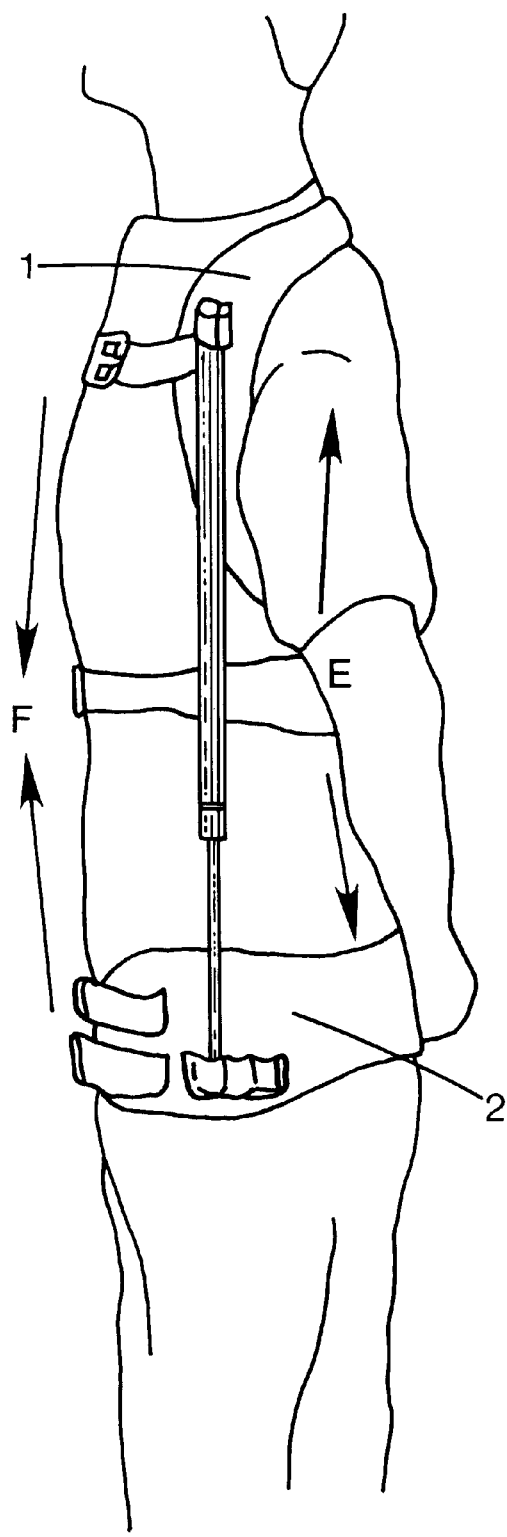
Figure 4:
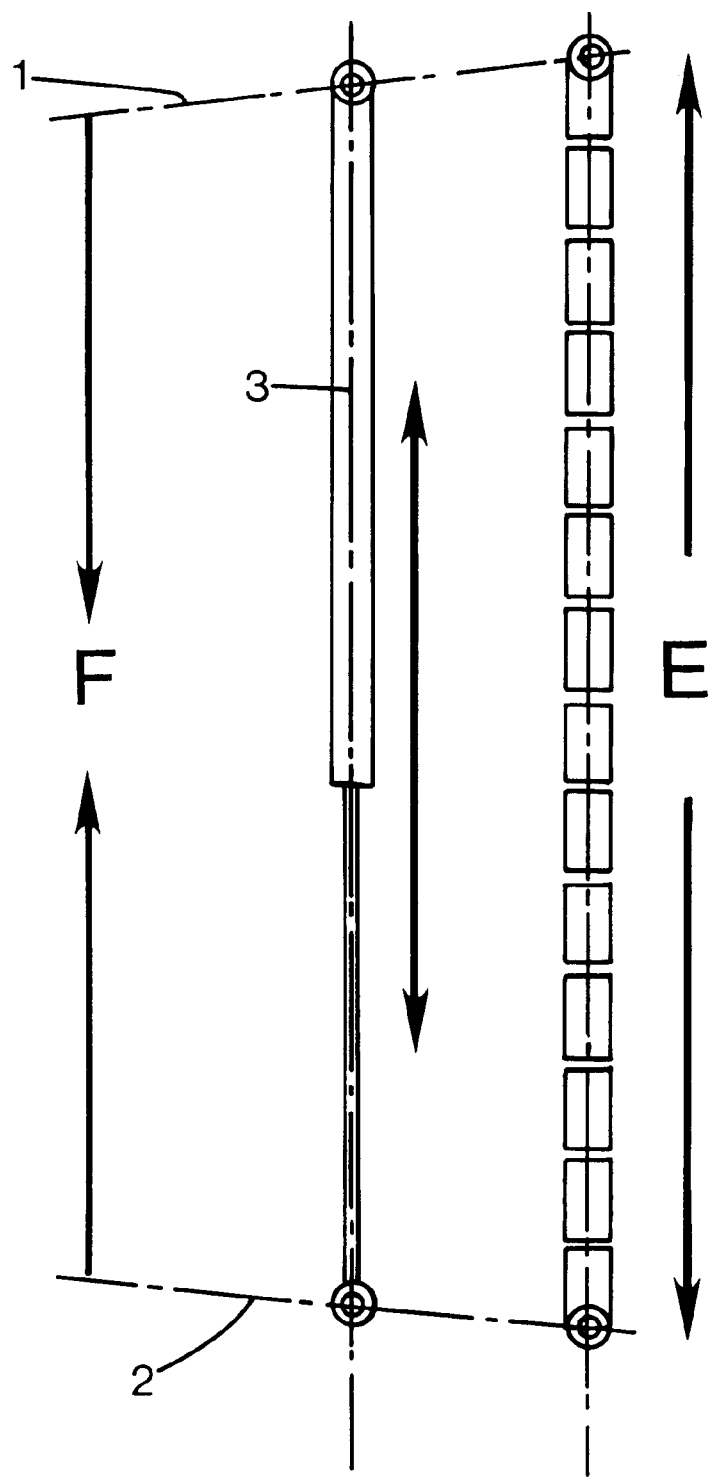

An embodiment example of the invention will be described below, with reference to the enclosed drawings, of which:

FIG. 1 shows a patient seen from the front, dressed in the device according to the invention, FIG. 2 shows the same patient, seen from behind, FIG. 3 shows the same patient again, but seen from the left hand side, and FIG. 4 shows, schematically, the interplay between pulling forces from the abdominal muscles and the device according to the invention, in a preferred embodiment.

FIGS. 1 and 2 show all main components of the device according to the invention. An upper chest and shoulder harness 1 is provided, to be fastened tight around the chest of the patient so as to act and support directly at the patient's armpits. The harness is, in the shown embodiment, fastened over the breastbone by being drawn around the back just below the shoulder blades and being tightened with a belt buckle 9.

The adaptation to the chest and shoulder shape of the patient is made by adjustment of the lengths of the adjusting belts 5 and 6 with their belt buckles 15 and 16. This harness attacks as high up on the spinal column as possible, up towards the T:1 to T:5 vertebrae, by engaging shoulders and keybones and pushing them upwards, and functions as an upper mounting for the elastic force elements which are to provide the traction.

A lower hip/pelvis harness 2, similar to an old-fashioned so called body belt, is provided, to be attached over the patient's hipbone or iliac crests by means of belts 9 and belt buckles 19. This harness functions as the lower counterhold for the elastic force elements which are to provide the traction, and it thus engages so far down that the vertebrae all the way down to L:5 will be subjected to traction.

Both harnesses are preferably made from chrome-free, tanned leather, for anti-allergic reasons.

The elastic force elements 3 consist of as such known gas-filled piston-and-cylinder arrangements of the type called 'gas springs', which are commonly used for aiding in the lifting of heavy boot lids on passenger cars and similar. For this application, a kind of such gas springs having a low internal friction is preferably used. Such gas springs 3 show the important advantage in this connection, that their spring force, which may for this purpose be in the order of 50 to 100 N each, contrary to the mechanical springs of the known devices, will vary very little with the stroke, only about ±10%, in spite of the strokes in this case being relatively long, about 250 mm. This should be compared to the force variations for the corresponding mechanical springs, where the force change for the corresponding change in length (250 mm) would normally be about ±100%.

The gas springs 3 are selected, regarding spring force, in dependence of the patient and the ailment. One gas spring is normally attached on each side of the body symmetry plane S, passing through the spine, by means of mountings 7 on the lower harness and mountings 8 on the upper harness, in such a way that when the patient is standing upright, the gas spring 3 must be compressed between about 20% and 35% of their full stroke. The mountings 7 and 8 are designed similarly to the pockets of a gun belt, with the difference that they are provided with a strongly sewed-on bottom and top, respectively, to take up the longitudinal pushing forces from the gas springs and transfer them to the harnesses. The most common and preferred way of attaching the gas springs 3, is first to push their rod end down into one of the mountings 7 on the lower harness 2. You then take a firm hold on the barrel of the gas spring 3 and compress it downwards until the barrel end can be slipped into the corresponding mounting 8 on the upper harness 1. The process is then repeated symmetrically on the other side of the patient. The traction has now commenced.

It is also conceivable to have an embodiment where the barrel ends of the gas springs 3 are entered into the lower pocket 7 or upper pocket 8 respectively, protruding through a smaller hole in the bottom, or top, respectively, of the respective pocket, and being fastened by a domed nut being screwed onto the protruding threaded end in such a way that the gas spring will always be attached to one of the harnesses. Said barrel end is then always fastened first. In order to obtain a better grip on the rod end when compressing the gas spring and fitting it into the other mounting (8 or 7 respectively), this end is then provided with a leather strap looped through the rod eye.

The lower mountings 7 are designed like a row of identical, adjacent mountings on each side of said symmetry plane S, partly for allowing adaptation of the lower harness to the varying abdomen and pelvis measurements of different persons, partly for allowing a certain variation in the characteristics of the apparatus when bending the body toward the sides or forward, respectively.

Also on the top harness 1, there are, for the same reasons, at least two mountings 8, on each side of the symmetry plane S.

Gas springs 3 are available within a sufficiently large span of force, so that in most cases it is possible to make do with one gas spring on each side of the symmetry plane S. The multitude of mountings provided on the device however, make it possible to use more than two gas springs on the same patient, if that would be necessary for reasons of treatment, or reasons of logistics, like stockholding etc.

In an embodiment being especially suitable for persons who are allowed to, and recommended to, actively train their abdominal muscles, and are at the same time allowed to apply a momentarily increased traction onto their spinal column, the gas springs 3 are placed in such a way that their projection in said symmetry plane, when seen perpendicularly thereto, lies between the spinal column and the longitudinal abdominal muscles, see FIG. 3. Upon contraction of the abdominal muscles, as shown by the arrows F, in order to bend forward against the counteracting force from the two gas springs 3, the bending centre of the body will move forward from the spine, therefore causing the traction on the spinal column, as shown by the arrows E, to increase very effectively in the process.

For some afflictions, bending forward is instead unsuitable, and consequently, the gas springs are located as far to the front side of the body as possible, to increase the forward bending resistance.

Thanks to the superior spring characteristics of the gas springs 3, with the above-mentioned small changes in force for changes in the distance between the mountings 7 and 8, the treatment force determined and adjusted by the doctor or the therapist will always be nearly constant, also when the location of the harnesses vary somewhat depending on how the patient or the attendants place the harnesses 1 and 2 when fitting them. For the same reasons, no adjustment of length is required for persons having different torso lengths, which simplifies the use. Furthermore, the size of the force will not be significantly influenced when the patient e.g. bends sideways.

As the gas springs 3 are located at the front of the body, the patient will be able to rest comfortably on his/her back during treatment, should this be required or wanted by the patient.

The device may also, thanks to the location of the gas springs at the front of the body, be used for straightening treatment on persons having a forward bent posture.

As the device may be carried without major infringement of the bearer's comfort or freedom of movement also in a seated position, it is also suitable for relief of the spinal column of persons with back trouble working in vibrating vehicles, such as dumpers or excavators, for preventive as well as for medical treatment purposes.

The present device is especially suitable for treatment of lumbago, scoliosis, vertebral displacement, and against vertebrae and disc compression in the spine. It is also very suitable for persons having had an operation of the spinal column, and which are otherwise not allowed to apply load to it without special aids, like gangways, etc.

From the above description, it should be evident that the present invention provides an improved device for traction and relief of the spinal column, improving the function and reducing the force variations, allowing a largest possible section of the spinal column, from the region around T:1–T:5 all the way down to L:5, to be stretched, making the device easier to adjust and to put on and needing less precision to achieve the correct traction force, allowing self-traction through contraction of the patient's abdominal muscles, and being lighter an more comfortable to carry in a standing, sitting as well as a lying position.

The device is by no means limited to the preferred embodiment described herein, but can be varied within the scope of the accompanying patent claims. For example, the belt buckles 19, 15 and 16 may conceivably be replaced by a so called Velcro fastenings, and the harnesses may be made from another suitable material than leather.

What is claimed is:

1. A device for applying traction to and applying a tension force on a patient's spinal column, the patient having a hip bone, shoulders and a chest, comprising:
   a lower adjustable harness supported by the patient's hip bone, the lower harness having a front side;
   an upper adjustable harness supported around the patient's chest and shoulders, the upper harness having a front side; and
   gas pistons having one end attached to the front side of the lower harness and an opposite end attached to the front side of the upper harness, the gas pistons being biased to separate the lower harness from the upper harness, each gas piston being symmetrically disposed on each side of the spinal column, the gas pistons providing a spring force that is substantially independent of a stroke length of the gas pistons, the upper harness providing an upwardly directed force against the patient's shoulders.

2. The device according to claim 1 wherein the gas pistons are substantially parallel to the spinal column for providing a tension force on the spinal column.

3. The device according to claim 1 wherein the gas pistons are substantially parallel to one another.

* * * * *